US009144651B2

(12) United States Patent
Stuart (10) Patent No.: US 9,144,651 B2
(45) Date of Patent: Sep. 29, 2015

(54) DOSE COUNTER (75) Inventor: Adam J. Stuart, Loughborough (GB)

(73) Assignee: 3M Innovative Properties Company, Saint Paul, MN (US)

(*) Notice: Subject to any disclaimer, the term of this patent is extended or adjusted under 35 U.S.C. 154(b) by 600 days.

(21) Appl. No.: 13/509,620

(22) PCT Filed: Nov. 18, 2010

(86) PCT No.: PCT/US2010/057135
§ 371 (c)(1),
(2), (4) Date: May 14, 2012

(87) PCT Pub. No.: WO2011/063067
PCT Pub. Date: May 26, 2011

(65) Prior Publication Data
US 2012/0234317 A1 Sep. 20, 2012

(30) Foreign Application Priority Data

Nov. 23, 2009 (GB) .................................. 0920499.1

(51) Int. Cl.
*A61M 11/04* (2006.01)
*A61M 15/00* (2006.01)
*G06M 1/04* (2006.01)
*G06M 1/24* (2006.01)

(52) U.S. Cl.
CPC ......... *A61M 15/009* (2013.01); *A61M 15/0073* (2014.02); *A61M 15/0075* (2014.02); *G06M 1/041* (2013.01); *G06M 1/24* (2013.01)

(58) Field of Classification Search
CPC ....... G06M 1/04; G06M 1/041; G06M 1/083; G06M 1/163; A61M 15/009; A61M 15/0068; A61M 15/0071; A61M 15/0073; A61M 15/0075; A61M 15/0076; A61M 15/0078
USPC ............ 128/200.11, 200.12, 200.13, 200.14, 128/200.15, 200.16, 200.17, 200.18, 128/200.19, 200.21, 200.22, 200.23, 128/200.24, 203.12, 203.15, 205.23
See application file for complete search history.

(56) References Cited

U.S. PATENT DOCUMENTS

| 5,349,945 | A | 9/1994 | Wass et al. | |
| 5,871,007 | A | 2/1999 | Clark, Jr. | |
| 6,752,153 | B1 | 6/2004 | Eckert | |
| 2007/0246042 | A1* | 10/2007 | Purkins et al. | 128/200.14 |
| 2009/0173346 | A1* | 7/2009 | Stuart et al. | 128/203.12 |
| 2010/0229857 | A1* | 9/2010 | Von Schuckmann | 128/200.23 |
| 2011/0259324 | A1* | 10/2011 | Hochrainer | 128/200.14 |

FOREIGN PATENT DOCUMENTS

| DE | 10 2006 049 614 | 4/2008 |
| GB | 2 372 541 | 8/2002 |
| WO | WO 93/24167 | 12/1993 |
| WO | WO 98/56444 | 12/1998 |
| WO | WO 99/36115 | 7/1999 |
| WO | WO 99/57019 | 11/1999 |
| WO | WO 00/59806 | 10/2000 |
| WO | WO 2004/041334 | 5/2004 |
| WO | WO 2005/060535 | 7/2005 |
| WO | WO 2006/062450 | 6/2006 |

(Continued)

*Primary Examiner* — Annette Dixon
*Assistant Examiner* — Elliot S Ruddie (57) ABSTRACT Described are a dose counter (200) for use with an inhaler (5), and an actuator (20) for use with or as part of a dispenser. Further described is a dispenser containing a dose counter.

15 Claims, 6 Drawing Sheets (56) References Cited

FOREIGN PATENT DOCUMENTS

| WO | WO 2007/124406 | 11/2007 |
| WO | WO 2009/037085 | 3/2009 |
| WO | WO 2011/071788 | 6/2011 |

* cited by examiner

DOSE COUNTER

CROSS REFERENCE TO RELATED APPLICATIONS

This application is a national stage filing under 35 U.S.C. 371 of PCT/US2010/057135, filed 18 Nov. 2010, which claims priority to United Kingdom Application No. 0920499.1, filed 23 Nov. 2009, the disclosure of which is incorporated by reference in its/their entirety herein.

FIELD OF INVENTION

This invention relates to dose counters for dispensers and in particular to dose counters for use with metered dose inhalers comprising a container for medicament equipped with a reciprocal actuation means, such as a valve, to dispense a dose of medicament from the container.

BACKGROUND

Since the metered dose pressurised inhaler was introduced in the mid-1950's, inhalation has become a widely used route for delivering bronchodilator drugs and steroids to the airways of asthmatic patients. More recently, inhalation from a pressurised inhaler has been a route selected for administration of other drugs that are not primarily concerned with treatment of a bronchial malady.

A pressurised metered dose inhaler generally comprises an aerosol container equipped with a metered dose dispensing valve (which is generally herein referred to as a canister) and an actuator. The actuator generally comprises a nozzle block to retain the canister (typically the valve stem of the metering valve) and a user-port such as a mouthpiece, as well as an optional, but typically used, cylindrical housing for housing the aerosol container. The aerosol container contains a pressurised aerosol formulation that generally comprises a liquefied propellant and a medicament and, if desired and/or needed, one or more excipients such as a surfactant or a solvent. The medicament may be in the form of a dispersion or in solution in the aerosol formulation. Metered dose dispensing valves generally comprise a valve stem that is moved inwardly with respect to the container to dispense a metered dose of aerosol formulation. The canister is inserted into the actuator with the valve stem engaging the nozzle block of the actuator. In use, a patient places their lips round the mouthpiece and presses the base of the aerosol container causing the container to move relative to the valve stem to fire a dose of medicament through the mouthpiece.

One of the disadvantages arising from the use of such known inhalers is that the patient cannot readily determine the amount of medicament in the container at any given time. In an extreme case this could mean that a patient in need of a dose of medicament might find that the inhaler will not dispense a dose because its contents have already been exhausted.

There have been many proposals for dose counters for use with metered dose inhalers, in particular pressurised metered dose inhalers, including e.g. dose counters described in DE 10 2006 049 614 (RPC Formatec GmbH), WO 2000/059806 (Allsop et al.), WO 1998/056444 (Rand et al.), WO 2005/060535 (Purkins et al.), WO 2007/124406 (Stuart et al.) and WO 1993/024167 (Holroyd). Some are mounted onto the base of the aerosol container (e.g. WO 1993/024167), some are mounted onto the ferrule of the aerosol container (e.g. WO 1998/056444) and others are retained within the interior of the actuator beneath the aerosol container in the space near and or around the nozzle block (e.g. WO 2007/124406 and WO 2005/060535).

SUMMARY OF INVENTION

Incorporation of the type of dose counters retained within the interior of the actuator beneath the aerosol container in the space near and or around the nozzle block is generally advantageous in that the use of such dose counters can allow for the provision of an inhaler without any change—other than the provision of a dose-indication—from the perspective of the users, said users often being quite conservative and anxious towards any change. Moreover a dose counter retained within the interior of the actuator can allow for the provision of an inhaler without any change in form or size. Another advantage of actuator-retained dose counters is that they are less prone to being tampered with by the user or to suffer accidental damage. Further, the user of such an inhaler can use the inhaler as before, e.g. administering doses, removing the canister from the actuator as needed and/or desired to wash the actuator, washing the actuator, and re-inserting the canister into the actuator. However it has been found that for some actuator-retained dose counters, in particular those including a counter-ring and a count-indicating ring where the two rings are typically engaged, washing with tap water (e.g. hard tap water) in some instances can lead to accumulations such that the proper operation of the rings can be hindered, potentially leading to an undesired miscount or failure to count. It has been found that by configuring and arranging the counter ring and count-indicating ring such that during a first movement of the counter ring, the count-indicating ring undergoes an essentially transversing movement, accumulations formed between the two (e.g. nested) rings can advantageously be typically broken away, thus allowing for a smooth, desired operation of the dose counter.

Accordingly one aspect of the present invention provides a dose counter for use with an inhaler comprising a container for medicament equipped with a reciprocal actuation means to dispense a dose of medicament therefrom, the dose counter comprising; a counter member constructed and arranged to undergo a predetermined counting motion each time a dose is dispensed, the counting motion comprising at least a first vertical or essentially vertical movement; a count-indicating member constructed and arranged to undergo a predetermined count-indicating motion each time a dose is dispensed, the count-indicating member comprising a first region for interaction with the counter member; wherein the counter member comprises a first region for interaction with the count-indicating member, said first region of the counter member comprising at least one surface that is engaged with at least one surface of said first region of the count-indicating member; and wherein said first region of the counter member and said first region of the count-indicating member are configured and arranged, such that said count-indicating member completes its count-indicating motion in coordination with the counting motion of said counter member and during and induced by said first movement of the counter member the count-indicating member undergoes a rotational or essentially rotational movement.

By configuring and arranging the two members such that the count-indicating member undergoes a first rotational or essentially rotational movement at some time during the first movement (said movement being either vertical or essentially vertical) of the counter member, any accumulations between the two members may be easily and effectively broken away. In particular the first movement of the counter member favourably occurs under a force external to the dose counter, e.g. under force exerted by the user. This is favourable in that the first rotational or essentially rotational movement of the count-indicating member—being induced by said first movement of the counter member—occurs under said force, and thus any further bonding of or accumulation of material around the count-indicating member may be effectively broken or dislodged before committing to the dose count, thereby further facilitating the reliability of the dose counter and further reducing any tendency, due to washing with e.g. hard tap water, of a dose counter to fail to count.

A further aspect of the present invention includes an actuator for use with or as part of a dispenser, said actuator comprising a dose counter as described herein. Favourably the dose counter is mounted within the interior of the actuator.

Other aspects of the present invention include a dispenser comprising a dose counter as described herein and a dispenser comprising an actuator as described herein. Favourably such a dispenser may be a metered dose dispenser, more favourably a metered dose inhaler, and most favourably a pressurised metered dose inhaler.

In particular favoured embodiments of pressurized metered dose inhalers comprising dose counters as described herein, desirably the dose counter is mounted within the interior of the actuator such that in use, the dose counter is generally positioned beneath the aerosol container (or the canister including said container and metering valve) and/or around a nozzle block of the actuator.

Other favoured embodiments will be apparent from the dependent claims.

The above summary of the present invention is not intended to describe each disclosed embodiment or every implementation of the present invention. The description that follows more particularly exemplifies illustrative embodiments.

BRIEF DESCRIPTION OF DRAWINGS

By way of example only, embodiments of the present invention will now be described below with reference to the accompanying drawings.

FIGS. 2 (a) to (f) provide diagrammatic representations of the general underlying operation as well as the configuration and arrangement of certain elements of a dose counter in accordance with the present invention. FIGS. 2(b) to (e) show positions therebetween.

DETAILED DESCRIPTION

It is to be understood that the present invention covers all combinations of particular, suitable, desirable, favourable, advantageous and preferred aspects of the invention described herein.

Figure 1:
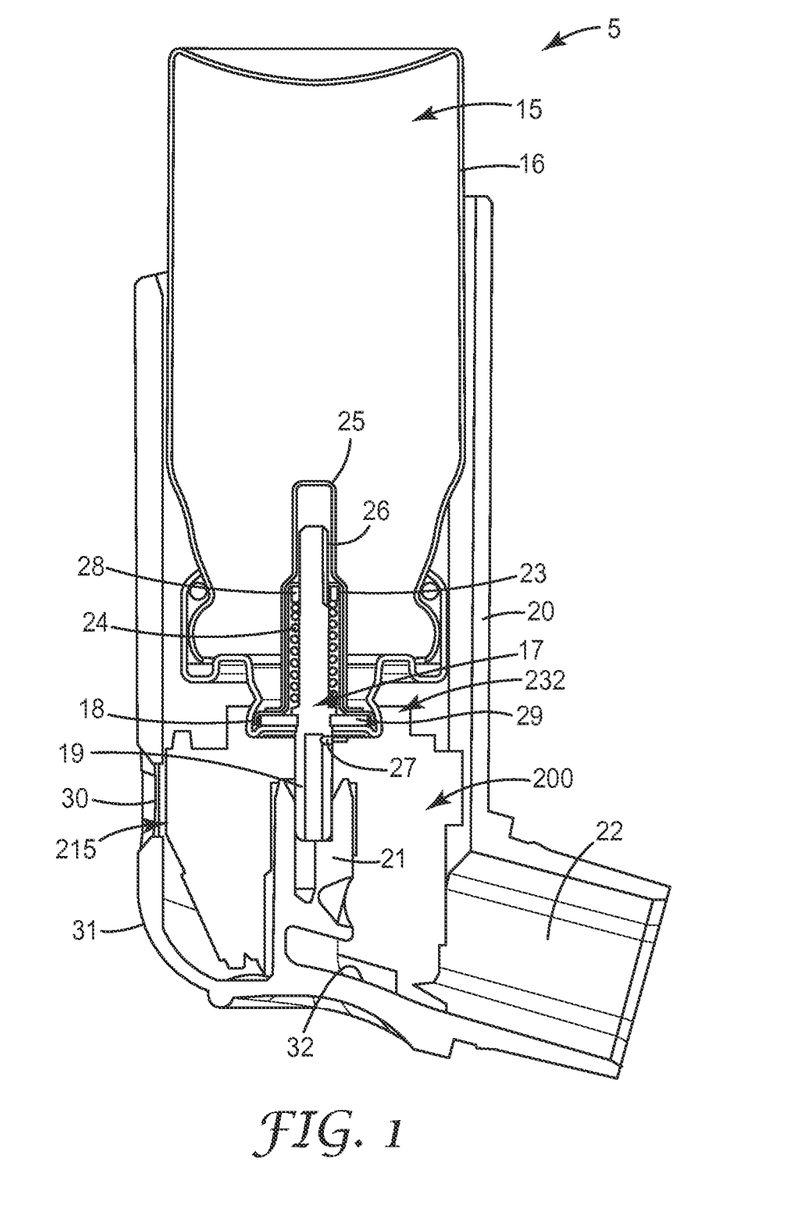
FIG. 1 is a schematic, and in part diagrammatic, illustration of a vertical cross-section through an exemplary pressurized metered dose inhaler.

For better understanding of the present invention, an illustrative, exemplary pressurized metered dose inhaler will be first described. FIG. 1 provides a schematic illustration of a vertical cross-section through an exemplary pressurized metered dose inhaler (5). The illustrated pressurised metered dose inhaler (5) comprises the following components: a canister (15), an actuator (20) and a dose counter (200). The dose counter is only shown diagrammatically showing its outer profile in an outline form, and advantageously it is a dose counter in accordance to the present invention, in particular the exemplary dose counter illustrated in FIG. 3 (discussed in detail infra)). The canister (15) includes an aerosol container (16) equipped with a metering valve (17) secured via a ferrule (18). The metering valve (17) includes inter alia a valve stem (19), generally a valve body (23) defining a metering chamber, and a spring (24). The metering valve (17) may also include an outer valve body (25) serving as a bottle emptier and/or defining a pre-metering chamber. Although not shown in the illustration, the container (16) typically contains an aerosol formulation that generally comprises at least one active agent (such as at least one medicament) and liquefied propellant (e.g. HFA 134a and/or HFA 227), and optionally one or more excipients. The actuator (20) and canister (15) are arranged so that the valve stem (19) engages with a nozzle block (21) provided within the actuator so that the canister is thus retained in the actuator. In use (when the aerosol container indeed contains a medicament aerosol formulation), the user actuates the pressurized metered dose inhaler (5) to dispense a single dose of medication via the mouthpiece (22) by pressing down on the container (16). Due to the fact that the valve stem (19) is held fixed by the nozzle block and the container (16) moves downwardly when the user presses down on it (thus compressing the valve spring (24)), there is a relative reciprocal movement between the metering valve stem and the container. On this actuation (outward) stroke, once the container moves sufficiently downwards an inner groove (26) of the valve stem (19) passes an inner gasket seal (28) so that the metering chamber is sealed off, and once the container moves further sufficiently downwards an opening (27) of the outer portion of the valve stem (19) passes an outer gasket (29) into the metering chamber so that the metering valve will fire (dispense) a metered dose of medicament containing formulation (i.e. that quantity of formulation in the metering chamber). After actuation, once the user releases the container, the container on its return stroke will move (under the force of the expansion of the valve spring) upwardly relative to the valve stem back to its position of rest. It will be appreciated that over time and use of an inhaler, it can be desirable to clean the mouthpiece. To clean the mouthpiece (22), generally the user of the inhaler will wash the actuator (20) with tap water after removing the canister (15) from the actuator (20), a process that involves withdrawing the valve stem (19) from the nozzle block (21). After washing and drying, the canister (15) is re-fitted in the actuator. As illustrated, the dose counter (200) is mounted within the interior of the actuator (20), generally positioned beneath the container near and around the nozzle block (12), where the count may be viewed through a window (215) in the dose counter and a window (30) in the actuator back wall (31). The dose counter once mounted desirably remains in position within the actuator, even when the canister (15) is removed, so that the dose counter may not be removed by the user of the inhaler. As indicated supra, dose counters in accordance with the present invention are advantageously designed and constructed in a way that allows them to be washable (in particular washable with tap water), i.e. they can withstand several, in some cases more than ten, washing and drying cycles, while maintaining desirable dose counting performance.

Dose counters in accordance with the present invention comprise a counter member and a count-indicating member. The counter member is constructed and arranged to undergo a predetermined counting motion each time a dose is dispensed, the counting motion comprising at least a first vertical or essentially vertical movement and the count-indicating member constructed and arranged to undergo a predetermined count-indicating motion each time a dose is dispensed, the count-indicating member comprising a first region for interaction with the counter member. The counter member comprises a first region for interaction with the count-indicating member, said first region of the counter member comprising at least one surface that is engaged with at least one surface of said first region of the count-indicating member and the first region of the counter member and said first region of the count-indicating member are configured and arranged, such that said count-indicating member completes its count-indicating motion in coordination with the counting motion of said counter member and during and induced by said first movement of the counter member the count-indicating member undergoes an essentially rotational or rotational movement.

Before turning to a specific exemplary embodiment of a dose counter in accordance to the present invention and illustrated in FIGS. 3 to 6, the general underlying configuration and arrangement including the operation of a dose counter in accordance with the present invention (in particular a counter-member and a count-indicating member thereof) will be described using diagrammatic representations provided in FIGS. 2(a) to (f). For clarity of explanation and to allow easier understanding of functionality, FIG. 2 shows schematic, limited and partial representations of a counter-member and a count-indicating member, where the counter member is the element labelled 240 and the count-indicating member is the element labelled 250. The illustrations also show additional elements labelled 224 and 230, which are a fixed ratchet member and an indexing member, respectively; once again both elements being shown partially and schematically. The line labelled "A" represents the longitudinal axis of reciprocal movement between the actuation means (e.g. metering valve) and the container (e.g. aerosol container) of an inhaler. It is noteworthy that the vertical surface (225) of the fixed ratchet member (224) is positioned in line with line A as viewed in FIGS. 2(a) to (f), thus facilitating a comparison of horizontal movements (e.g. rotational movements) of the illustrated counter member and count-indicating member over the series of FIGS. 2(a) to (f) showing relative positions during a dose counting cycle.

The count-indicating member (250) includes a region for interaction and engagement with the counter member (240). In particular the count-indicating member includes at least one channel (256), more particularly at least one inclined channel. As can be seen in FIG. 2 the aforementioned at least one inclined channel is angled relative to the longitudinal axis A. Vertical movement of the count-indicating member (250) is favourably limited or essentially prevented e.g. by another element in the dose counter (not shown in FIG. 2).

During the dose counting cycle, and each time a dose is dispensed (described in more detail infra), the count-indicating member undergoes a predetermined indicating motion. In particular the predetermined count-indicating motion of the count-indicating member desirably includes only rotational or essentially rotational movements. It will be appreciated that due to engineering tolerances and a general desire to provide a relaxed fit of the count-indicating member within a counter to ensure smooth motion of the count-indicating member during its predetermined indicating motion, a count-indicating member may show some slight vertical movement during rotational movement ("essentially rotational movement").

The count-indicating member is favourably provided with an indicium or indicia e.g. for indicating how many doses or how much medicament is contained in the container and/or how many doses or how much medicament has been dispensed from the container, in particular said indicium or indicia being numeric and/or colour indicium or indicia.

The counter member (240) comprises a region for interaction with the count indicating member (250). In particular the counter member (240) comprises a protrusion (246) arranged for interaction and engagement with the count-indicating member (250). The illustrated protrusion (246) extends outwardly and has an essentially rectangular cross-section, where one corner edge (to the left in the illustration) of the protrusion engages an inner surface of the inclined channel (256) of the count-indicating member (250). Desirably, the protrusion (246) is a good fit in the inclined channel (256) with little clearance, and the opposite corner edge of the protrusion may also engage an opposite inner surface of the inclined channel (256).

During the dose counting cycle (described in more detail infra), the counter member undergoes a predetermined counting motion. In particular the predetermined counting motion of the counter member desirably includes, independently or simultaneously, vertical and horizontal (e.g. rotational or, if applicable, helical) movements, where the first movement is a vertical or essentially vertical movement. It will be appreciated that due to engineering tolerances and a general desire to provide a relaxed fit of the count member within a counter to ensure smooth motion of the count member during its predetermined counting motion, during its first vertical movement a count member may show some slight horizontal movement (e.g. rotational movement up to 4°, more desirably up to 2°) during vertical movement ("essentially vertical movement").

A dose counter favourably includes an indexing member constructed and arranged to undergo reciprocal movement coordinated with the reciprocal movement between the actuation means and the container and to induce at least the first vertical or essentially vertical movement of counter member (e.g. as shown in FIGS. 2(a) to (f)). The reciprocal movement of the indexing member (230) generally comprises an outward stroke and a return stroke. Favourably the counter member (240) comprises another region for interaction with the indexing member (e.g. a set of teeth (241) as shown in FIG. 2), where this region comprising at least one inclined surface which is engaged by the indexing member during its outward stroke causing the counter member to undergo the first vertical or essentially vertical movement (generally against a bias as discussed infra).

Figure 2A:
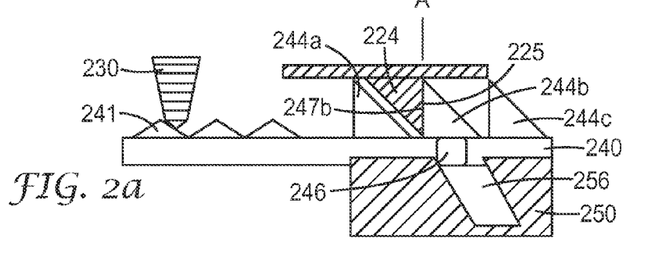
FIG. 2(a) shows the rest position prior to a count.

A dose counter may also favourably include a fixed ratchet member where the counter member then includes yet another region for interaction with the ratchet member, said region comprising at least one surface which is engaged by the ratchet member at the rest position of the dose counter (e.g. as shown in FIGS. 2(a) and (f)). In particular the at least one surface of this region of the counter member includes a vertical or essentially vertical surface. The counter member (240) may further comprise a (second) set of teeth (244a, 244b, 244c) where, as shown in e.g. FIG. 2(a), in the rest position a tooth (244b) is engaged with the fixed ratchet member (224). In particular a vertical surface (247b) of a tooth (244b) is engaged with the vertical surface (225) of the ratchet member (224). The engagement of the two vertical surfaces (247b and 225) prevents all but vertical or essentially vertical movement of the counter member.

As indicated supra, FIG. 2(a) shows the rest position prior to a count, while FIG. 2(f) represents a second rest position after the count. FIGS. 2(b) to (e) show positions therebetween.

Referring to the rest position prior to a count, represented by FIG. 2(a), the counter member (240) is at its uppermost extent of (vertical) travel. Generally the counter member (240) is favourably biased towards the ratchet member (224) (and even more favourably towards the indexing member (230)), in particular by at least one biasing element (not shown in FIG. 2), which may favourably comprise a spring, such as a coil spring or leaf spring. The ratchet member (224) typically prevents the counter member (240) from moving horizontally, e.g. since the vertical surface (247b in FIG. 2(a)) of the counter member tooth (244b in FIG. 2(a)) is also generally urged horizontally towards the vertical surface (225) of the ratchet member (224) by the first set of teeth (241) on the counter member (240) being biased upwards towards the indexing member (230) by the biasing element. Since the protrusion (246) of the counter member (240) is engaged with a surface of the inclined channel (256) of the count-indicating member (250), movement of the count-indicating member is also generally prevented with the counter member in its rest position. Although the indexing member (230) will typically be resting on a surface of a tooth of the first set of teeth (241) of the counter member (240) when the dose counter is in its rest position, it may alternatively be slightly distanced from it. In FIG. 2(a), the indexing member (230) is shown resting on the counter member (240).

Figure 2B:
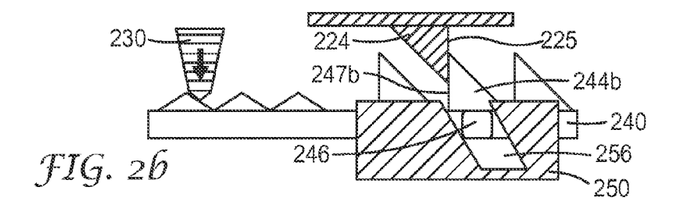
FIG. 2(b) represents a point in the dose counting cycle where the user of the inhaler has initiated the reciprocal actuation of a dose dispensing cycle.

FIG. 2(b) represents a point in the dose counting cycle where the user of the inhaler has initiated the reciprocal actuation of a dose dispensing cycle.

As already discussed supra for press-and-breath type pressurized metered dose inhalers (e.g. like that illustrated in FIG. 1), the dose dispensing cycle commences when a force is applied to the container by the user of the inhaler. Force resulting from this is desirably transmitted to the counter member via the indexing member inducing the first movement of the counter member. In particular the dose counter is favourably configured and arranged such that during actuation when the user presses down on the container, a part of the canister (e.g. the ferrule) contacts the indexing member inducing a movement (e.g. a vertical or essentially vertical movement) of the indexing member, and in turn the indexing member contacts (if not already in contact) the counter member and induces (at least) the first vertical or essentially vertical movement of the counter member.

It will be appreciated from a comparison of FIGS. 2(a) and (b) that, since the vertical surface (247b) of the tooth (244b) of the counter member (240) is still engaged by the vertical surface (225) of the ratchet member (224), horizontal (rotational) movement is essentially blocked and the indexing member (230) on its outward stroke in essence induces the counter member to move (essentially) vertically downwards. The (corner of the) protrusion (246) on the counter member (240) that is engaged with a surface of the inclined channel (256) of the count-indicating member (250), also moves (essentially) vertically downwards, causing the count-indicating member (250) to move horizontally (rotationally) towards the left (as drawn). Thus the first movement of the counter member is vertical or essentially vertical, and during this first movement of the counter member the count-indicating member undergoes a rotational or essentially rotational movement which is induced by the first movement of the counter member. As mentioned supra, these two first, transversing movements advantageously serve to break any bondings and/or accumulations (such as limescale) between the two (typically nesting, members) as well as to break any bondings and/or accumulations between the count-indicating member and any other parts of a dose counter (such as the outer housing) under the aid of force exerted by the user (transmitted via an indexing member) at the very start of dose dispensing.

Figure 2C:
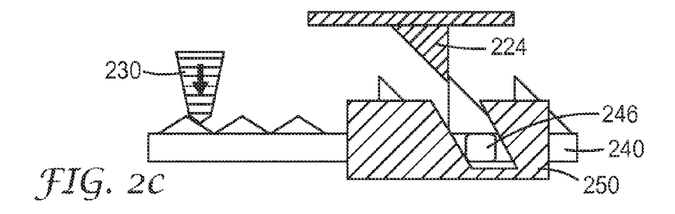
FIG. 2(c) shows the positions of the component parts just before disengagement occurs.
Figure 2D:
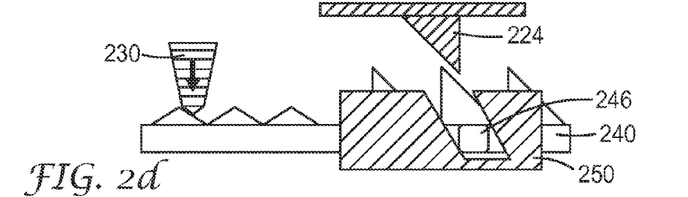
FIG. 2(d) shows a position shortly before the lowermost (vertical) extent of travel.
Figure 2E:
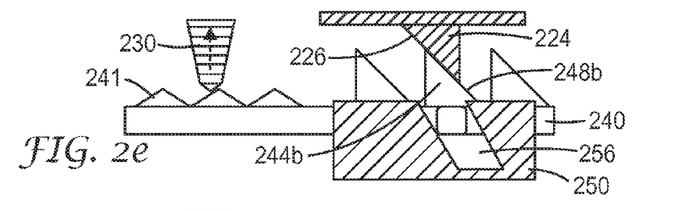
Figure 2F:
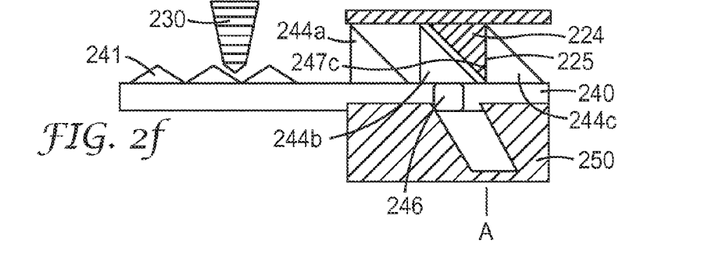
FIG. 2(f) represents a second rest position after the count.

FIGS. 2(c) to (e) represent the remaining pre-determined counting motion of the counter member as well as the coordinated, remaining pre-determined count-indicating motion of the count-indicating member, both returning then to a second rest position represented by FIG. 2(f).

As the downward force from the user on the container continues, the counter member (240) will continue to move (essentially) vertically downwards and the count-indicating member (250) will continue to move horizontally to the left until the ratchet member (224) disengages from the counter member (240). FIG. 2(c) shows the positions of the component parts just before this disengagement occurs. If the user relieves his force on the container before disengagement, the counter member (240) and the count-indicating member (250) will return to the first rest position as shown in FIG. 2(a), and no dose count will be recorded. If the force continues to the point where disengagement occurs, then a count of a dose will follow. Upon disengagement, there is no return to the first rest position, and a surface (226) of the ratchet (224) will engage with a surface (248b) of the tooth (244b) to complete the count, so that a full count will be recorded. Due to inter alia engineering tolerances it is normally difficult to have the points of no return of a dispensing cycle and a dose counting cycle synchronized, and thus generally the point of no return for a dose counter is typically purposely set to be earlier than that of the dispenser, so that there is normally a tendency to over-count rather than under-count. Accordingly typically after the point of no return for a dose counter, the user typically still needs to apply some more force on the container to cause actuation of the inhaler.

It will be appreciated e.g. from FIG. 2, that the release of the engagement of the counter member to the ratchet member allows for a subsequent, rotational or essentially rotational movement of the counter member under the force of the bias and, if applicable, further vertical movement downwards due to further outward stroke of the indexing member. Desirably the count-indicating member rotates essentially in tandem with the rotational or essentially rotational movement(s) of the counter member.

In particular, the illustration FIG. 2(d) shows a position as the user continues to press down on the container to cause actuation of the inhaler. (Generally an inhaler allows some relative movement between the valve stem and the valve body beyond the actuation (dose release) point.) As the force from the user continues, since the counter member (240) is no longer engaged to the ratchet member (224), the counter member (240) moves horizontally somewhat to the left (mainly under the force of the aforesaid bias (not shown in FIG. 2)) and further vertically downwards towards its lowermost extent of (vertical) travel (mainly under the force of the further outward stroke of the indexing member (230)). The position in FIG. 2(d) is shortly before the lowermost (vertical) extent of travel. During this movement of the counter member (240), the count-indicating member (250) moves horizontally further to the left and then stops when the protrusion (246) of the counter member "bottoms out".

Once the user releases his force on the container, the container moves outwardly relative to the nozzle block, and the metering valve returns to its rest position. Also as the container, and thus the ferrule, moves outwardly, the force on the indexing member is released allowing it to return to its rest position. Favourably the counter member includes a fourth region for interaction, said region being for interaction with the ratchet member and comprising at least one inclined surface that is engaged by the ratchet member during the return stroke of the indexing member. For example, in FIG. 2(e) the inclined surface (248b) of the tooth (244b) may represent such a region. The engagement of this fourth region with the ratchet member desirably causes the counter member to undergo further rotational and vertical movement to complete its predetermined counting motion. In particular, as represented in part by FIG. 2(e), the counter member (240) as well as the indexing member (230) moves vertically upwards under the force of the aforementioned bias (again not shown in FIG. 2). After an initial vertically upward movement, the inclined surface (248b) of the counter member tooth (244b) engages with the inclined surface (226) of the ratchet member (224) causing further horizontal movement towards the left as further vertically upward movement of the counter member (240) continues. Since the protrusion (246) on the counter member (240) is still engaged with the inclined channel (256) of the count-indicating member (250), the count-indicating member continues its horizontal movement. The respective movements of the counter member (240) and the count-indicating member (250) continue until a second rest position is reached, e.g. where the counter member reaches the uppermost extent of its (vertical) travel as shown in FIG. 2(f). During its return stroke, the indexing member (230) rides over one of the first set of teeth (241) during the upward vertical and horizontal movement of the counter member (240). It will be appreciated that under the force of the previously mentioned bias, the vertical surface (225) of the ratchet member (224) will typically be engaged with the vertical surface (247c) of the next tooth (244c) in the first series of teeth of the counter member (240) at the second position of rest (FIG. 2(f)).

Comparing FIGS. 2(a) and 2(f), it can be seen that the counter member (240) has incremented one count to the left, and likewise that the count-indicating member (250) has moved to the left to complete a dose count cycle. The counter and count-indicating members are now ready to commence their next pre-determined counting and count-indicating motions, respectively.

It will be appreciated that the counter member and the count-indicating member may be, independently, provided in various forms including rings, cylinders, disks or cones. It will also be appreciated that the two members may be nested.

As discussed above, each of the counter member and the count-indicating member comprises a first region for interaction with one another. The first region of the count-indicating member may comprise at least one channel while the first region of the counter member may then comprise at least one protrusion, wherein the at least one channel and the at least one protrusion are constructed and arranged such that at least one surface of said at least one protrusion engages with at least one surface of said at least one channel. (See for example the schematic illustrations of FIG. 2.) Alternatively the first region of the count-indicating member may comprise at least one protrusion while the first region of the counter member may then comprise at least one channel, wherein the at least one channel and the at least one protrusion are constructed and arranged such that at least one surface of said at least one protrusion engages with at least one surface of said at least one channel.

As mentioned supra the at least one channel is favourably angled relative to the longitudinal axis of reciprocal movement between the actuation means (e.g. metering valve) and the container (e.g. aerosol container). The at least one channel is more favourably angled at an angle of 1 degree up to and including 60 degrees relative to the aforesaid longitudinal axis. It has been found desirable in terms of frictional forces that an user needs to overcome and/or in terms of providing desirable first rotational movement, that it is desirable the at least one channel is angled at an angle of 10 degrees up to and including 45 degrees relative to the aforesaid longitudinal axis, more desirably 15 degrees up to and including 35 degrees, and most desirably 20 degrees up to and including 30 degrees.

An exemplary dose counter in accordance to the present invention will now be described, i.e. the dose counter (200) illustrated in FIGS. 3 to 5 and parts thereof in FIG. 6. For ease in comparing and correlating elements in FIGS. 3 to 6 to the general description provided above with the aid of the representations in FIG. 2, the same reference number is used for similar elements.

Figure 3:
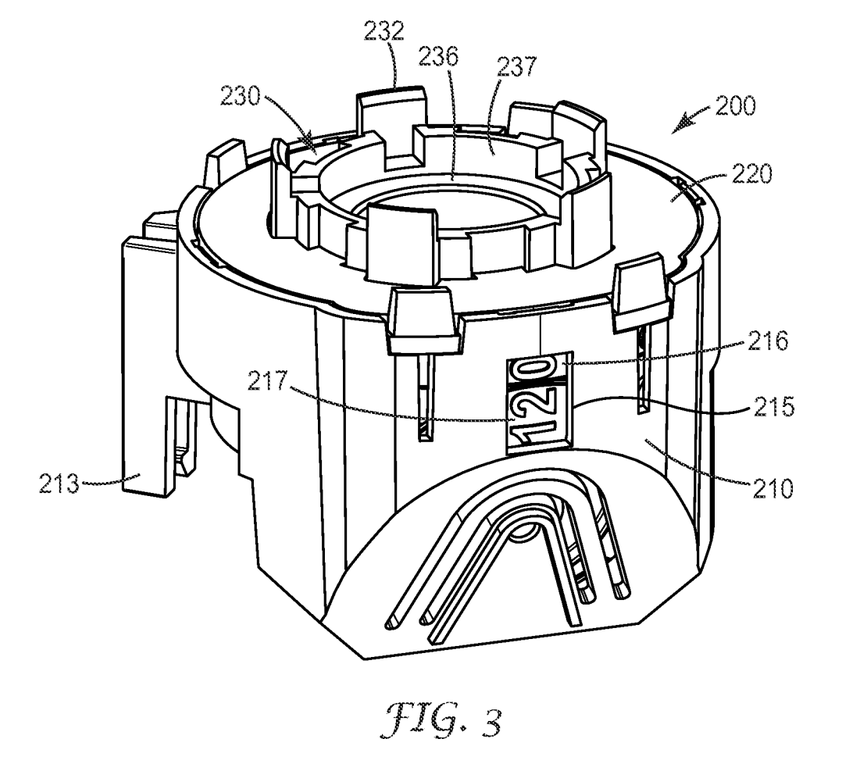
FIG. 3 is a perspective illustration of an exemplary dose counter in accordance with the present invention.

FIG. 3 is a perspective illustration of an exemplary dose counter in accordance with the present invention. As can be appreciated from FIG. 3, the working components of the dose counter (200) are contained within a housing (210) and retained by a lid (220), where essentially just indicia (216, 217) are visible via a window (215). Alternatively, the complete housing may be provided in a transparent material, such that the indicia may be viewed through the sidewall of the dose counter housing. The housing (210) and lid (220), inhibit the ingress of dust, fibres, fluff and other debris, however they do not provide a water proof seal, and consequently water may ingress into the internal workings of the dose counter when exposed to water, e.g. during washing of the actuator.

Figure 4:
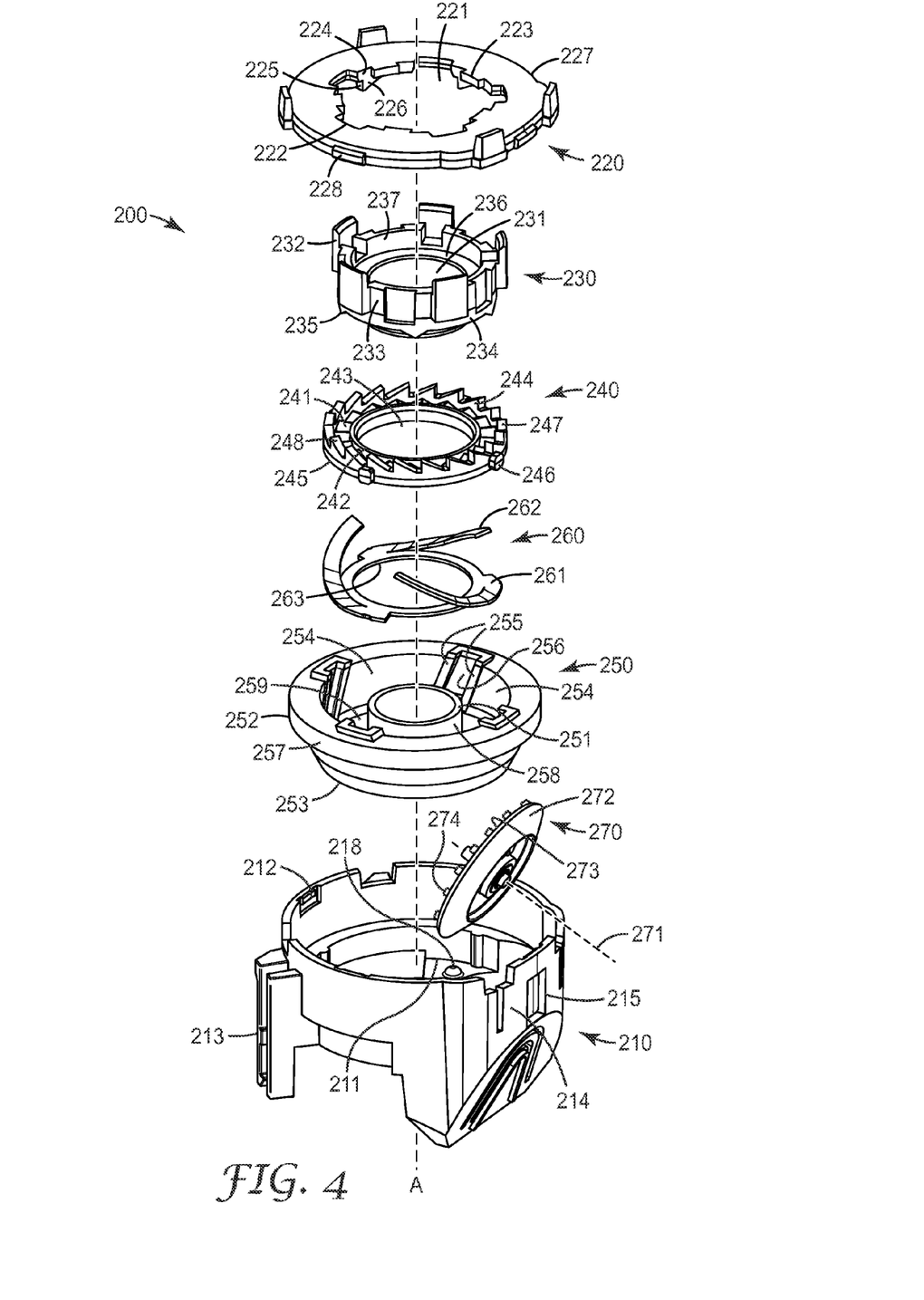
FIG. 4 represents an exploded view of the dose counter illustrated in FIG. 3.

FIG. 4 represents an exploded view of the dose counter (200) illustrated in FIG. 3, oriented about an axis A. When the dose counter is used in conjunction with an inhaler, such as the pressurized metered dose inhaler illustrated in FIG. 1, the axis A is along the longitudinal axis of reciprocal movement between the metering valve and the aerosol container. Besides the lid (220) and housing (210), the dose counter (200) comprises a counter member (240), a count-indicating member (250), an indexing member (230), a spring (260) and a tens cone (270). In the illustrated embodiment the counter member (240) and the count-indicating member (250) are favourably in the form of two nested rings as described in the following.

The counter member (240) is provided with at least four regions of interaction: a first with the count indication member; a second with the ratchet member(s); a third with the indexing member (in particular with saw-tooth protrusions thereof); and a fourth again with the ratchet member(s). In particular, the counter ring is provided with two rings of upstanding teeth around a central cylinder (242) with a central hole (243). An outer ring of teeth (244) is disposed for interaction and engagement with ratchet members (224) provided on the bottom surface of the lid (220). The teeth of the outer teeth ring (244) comprise two regions for interaction; one region is a vertical surface (247) (i.e. the counter member's second region of interaction), the other region is an inclined surface (248) (i.e. the counter member's fourth region of interaction). An inner ring of teeth (241) is arranged for interaction and engagement with the saw-tooth protrusions (235) on the indexing member (230) (i.e. the counter member's third region of interaction) during the outward stroke of the indexing member, and favourably also during the return stroke of the indexing member of the illustrated embodiment. A circumferential perimeter (245) of the counter ring (240) has a plurality of circumferentially equally spaced protrusions (246) extending outwards and having essentially rectangular cross-sections. The protrusions (246) are arranged for engagement and interaction with the count-indicating ring (250) (i.e. the counter member's first region of interaction).

The count-indicating ring (250) is generally in the form of inner (251) and outer (252) coaxial cylinders, joined by an annular base (253). A plurality of raised bearing features (218) (one shown in FIG. 4) are disposed on a shelf (211) in the housing (210), providing a low friction surface on which the count-indicating ring rests and rotates. An internal circumferential surface (254) of the outer cylinder (252) has a plurality of features. Each feature comprises a pair of inwardly facing inclined ribs (255) on either side of an inclined channel (256). The inclined channels are arranged for engagement and interaction with the corresponding protrusions (246) of the counter ring (240). The inner cylinder (251) of the count-indicating ring (250) has a diameter such that it slides axially inside the central cylinder (242) of the counter ring (240). The outer cylinder (252) has an outer cylindrical surface (257) bearing indicia (not shown in FIG. 4, labelled 216 in FIG. 3) for indicating dose counts of medication being dispensed from or remaining in a medicament canister. The outer circumferential perimeter (245) of the counter ring (240) is slightly smaller in diameter than the internal surface (254) of the outer cylinder (252) of the count-indicating ring (250), thus allowing both axial (vertical) and rotational movement of the counter ring (240) relative to the count-indicating ring (250). The count-indicating ring (250) is however generally limited to rotational movement by the means of its location within the housing (210).

The indicia may be in the form of a sequence of numbers either increasing in value or decreasing in value around the count-indicating ring. Alternatively, if desired, the dose counter may be a dose indicator. For example, a change of colour, for example from green to red may be used to indicate the relative level of the medicament in the container. In such cases, an indication of the medicament status is sufficient; however the dose indicator is still required to accurately count each dose dispensed. Other indicia will be known to a person skilled in the art.

If desired, a tens cone (270) may be used. The tens cone (270) has a series of indicia (217) (see e.g. FIG. 3) disposed about an external conical surface (272). The external conical surface (272) is arranged such that the surface carrying the indicia (217) is in the same plane as the surface carrying indicia (216) of the count-indicating ring (250) (see e.g. FIG. 3). The indicia (217) are orientated such at the point of closest proximity with the count-indicating ring (250), the indicia (216, 217) can be read as one number comprising digits from the count-indicating ring (250) and from the tens cone (270). The internal surface (273) of the tens cone is also generally conical (inversely) and is provided with a plurality of radial spokes (274). The radial spokes (274) are arranged such that they may interact with one of two bosses (not shown) on the outer circumferential cylinder (252) of the count-indicating ring (250), leading to the periodic incremental rotation of the tens cone (270). Further tens cone configurations are described in WO 2007/124406, to which reference should be made.

The lid (220) is generally annular with a central circular hole (221). The hole has a plurality of circumferentially equally spaced radial hole extensions (222) of slightly greater radius and a plurality of circumferentially equally spaced small radially inward protrusions (223). Around the central hole (221) on the bottom surface of the lid (220) are a plurality of ratchet members (224), comprising two regions for engagement and interaction with the counter ring (240); one region is a vertical surface (225) and the other region is an inclined surface (226). Disposed around the outer circumferential edge (227) of the lid (220) are a plurality of protrusions (228) that provide a means of correctly orientating and securing the lid (220) to the housing (210).

The indexing member (230) is shaped generally like a cylindrical cap with a central hole (231). The indexing member (230) has a plurality of peripheral castellations (232) that are designed to pass through the radial hole extensions (222) of the lid (220). The indexing member (230) also has a plurality of peripheral grooves (233) designed to accommodate the inward protrusions (223) of the lid (220). The combination of these features allows for axial (vertical) movement of the indexing member relative to the lid, while securing the indexing member within the counter. On a bottom circumferential edge (234) of the indexing member (230) a plurality of circumferentially equally spaced saw-tooth projections (235) are provided for interaction with the inner ring of teeth (241) on the counter ring (240). The upper portion of the indexing member includes a castellation-bearing wall (237) and a circumferential ridge (236) that define a sunken, cylindrical space (better seen in FIG. 3).

The spring (260) which provides a biasing means can be in the form of an annular leaf spring. The leaf spring (260) has an annular ring (261) with a plurality of spring elements (262) or leaves extending generally helically (coaxially with the ring) from radial projections on the circumference of the ring. The inner circumferential edge (263) of the leaf spring (260) is slightly larger in diameter than the outer surface (258) of the inner cylinder (251) of the count-indicating ring (250) such that the bottom surface of the leaf spring (260) engages with the top surface (259) of the annular base (253) of the count-indicating ring (250). The spring elements (262) are biased upwardly from the leaf spring (260) such that they engage with the bottom surface of the counter ring (240). The leaf spring (260) thus biases the counter ring (240) axially away from the annular base (253) of the count-indicating ring (250) and towards the saw-tooth projections (235) on the indexing member (230) and towards the ratchet members (224).

The dose counter housing (210) has a generally cylindrical body with a plurality of clip features (212) to engage with the protrusions (228) of the lid (220) to provide a means of securing the lid (220) to the housing (210). Two forward legs (213) (one shown) are provided for engagement of the dose counter (200) with an interior surface of an actuator (e.g. an actuator of the type illustrated in FIG. 1). The housing (210) is also generally coaxial with respect to the axis (A), and has a lateral shelf (211), comprising a central hole (not shown). The sidewall (214) of the housing (210) may have a viewing window (215) (see e.g. FIG. 3) such that the indicia (216, 217) can be observed. The dose counter housing (210) has an internal tapering housing section extending downwards below the viewing window (215), which is constructed and arranged to accommodate the tens cone (270) such that the tens cone (270) can rotated about an axis (271) angled generally diagonally to the axis (A) of the dose counter (200).

Figure 5:
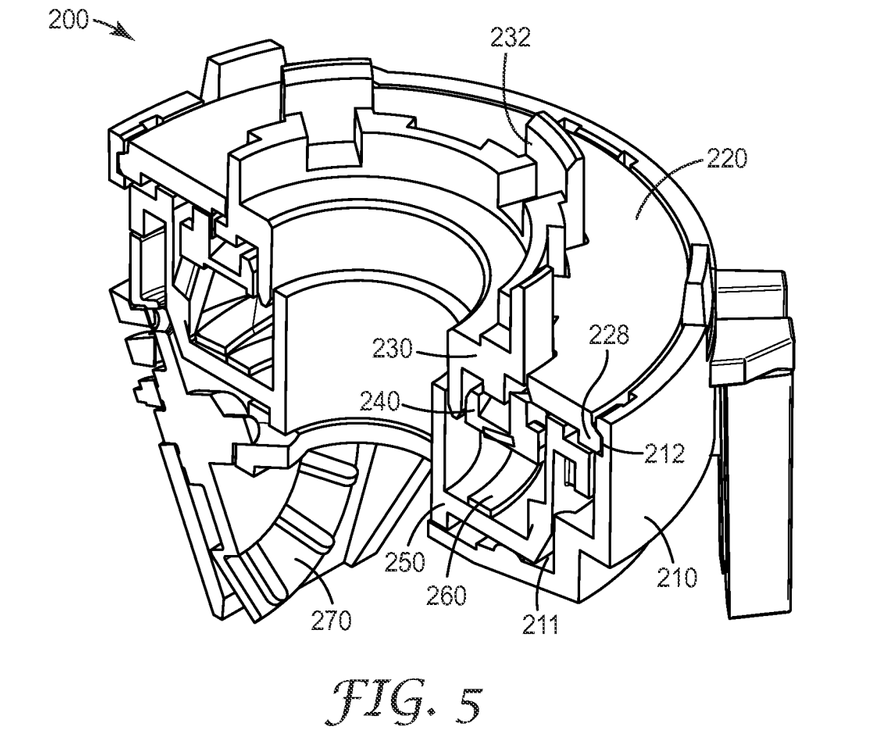
FIG. 5 shows a vertical cross-section, in a perspective view, of the dose counter illustrated in FIG. 3.

FIG. 5 shows a vertical cross-section of the assembled dose counter (200) shown in FIG. 3. The dose counter (200) may be assembled by inserting the tens cone (270) into the tapering housing section of the housing (210). The count-indicating ring (250) is then inserted and seated on the shelf (211) of the housing (210), above the tens cone (270). The leaf spring (260), counter ring (240) and indexing member (230) can then be assembled in order over the count-indicating ring (250), and the lid (220) fitted about the peripheral castellations (232) of the indexing member (230). As described above, the lid (220) is snap-fit engaged with the dose counter housing (210) by engagement of the protrusions (228) and associated clip features (212). The lid (220) and housing (210) may be otherwise connected together, such as by press fit connections, or may be ultrasonically or otherwise welded together.

Dose counters described herein are particularly advantageous for use with an actuator, the actuator being used with or as part of a dispenser, and/or for use with a dispenser (such as a metered dose dispenser, in particular a metered dose inhaler e.g. pressurized metered dose inhaler). Dose counters may be advantageously mounted within the interior of actuators, e.g. allowing for the desirable provision of washable actuators, in particular actuators washable with tap water. Such an actuator may be an actuator for use with a canister including an aerosol container and a metering valve and wherein the dose counter is mounted within the interior of the actuator, such that in use the dose counter is generally positioned beneath the container near and/or around the nozzle block of the actuator. For such actuators it is desirable that, in use, the dose counter is retained in the actuator when the canister is removed and the actuator washed.

The exemplary dose counter shown illustrated in FIG. 3 is particularly suitable for use in an actuator of a pressurized metered dose inhaler. Referring to FIG. 3 and FIG. 1, in particular the outlined profile form of the dose counter shown in FIG. 1 and the corresponding profile form shown in FIG. 3, it will be recognized that the dose counter (200) of FIG. 3 may be suitably mounted within the interior of the actuator (20) generally positioned beneath the container (16) near and around the nozzle block (21) of the actuator. Further it can be recognized that the window (215) in the counter housing (210) may face the window (30) in the back wall (31) of the actuator (20) and that the castellations (232) of the indexing member (230) may surround the ferrule (18). The ferrule may then be located within the sunken, cylindrical area defined within the castellation bearing wall (237) and circumferential ridge (236). Although not apparent from FIG. 1, the legs (213; one visible in FIG. 3) of the dose counter (200) may suitably engage with the bottom floor (32) of the actuator (20).

The operation of the dose counter illustrated in FIG. 3 with a pressurized metered dose inhaler such as that shown in FIG. 1 can be described as follows as.

Figure 6A:
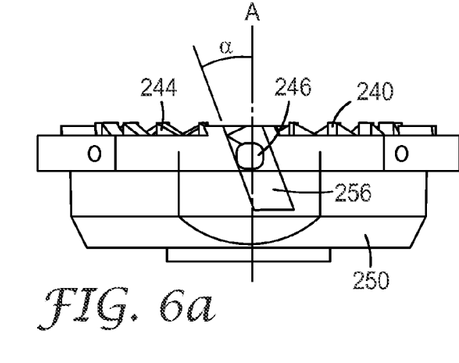
FIGS. 6(a) to 6(f) show the relative positions of the counter ring and count-indicating ring of the dose counter illustrated in FIG. 3, at a rest position (FIGS. 6a and 6b); at an intermediate position (FIGS. 6c and 6d) and at a further position during dose counting (FIGS. 6e and 6f).
Figure 6B:
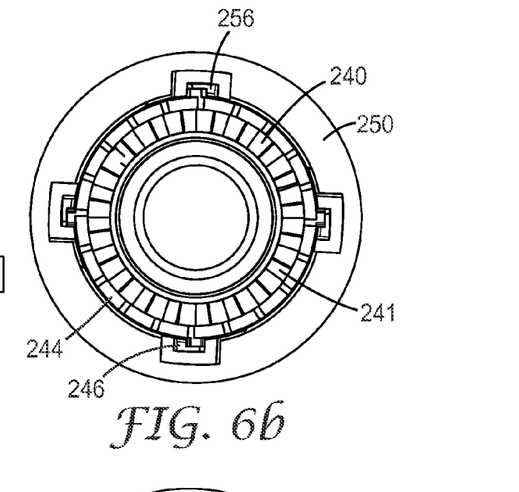

At the rest position of the dose counter (200), the vertical surfaces (225) of the ratchet members (224) disposed on the bottom surface of the lid (220) are engaged with the vertical surfaces (247) of the outer ring of teeth (244) on the counter ring (240). Also, the protrusions (246) on the outer perimeter of the counter ring (240) are engaged with the inclined channels (256) on the interior side of the outer cylinder (252) of the count-indicating ring (250). The protrusions (246) are arranged such that at least one corner of the protrusion is engaged with at least one inner surface of the inclined channel (256). As can be recognized from FIG. 6, desirably the protrusion corner that is positioned away from the ratchet member and in the direction that the counter ring will rotate is engaged with the at least one inner surface of the inclined channel. FIGS. 6(a) and (b) show the relative positions of the counter ring (240) and the count-indicating ring (250) at the rest position of the dose counter: (a) viewed from the side where the count-indicating ring is in part sectioned to show better the channel and (b) viewed from the top. Referring to FIG. 6(a), the inclined channel (256) is favourably inclined at an angle (α) of about 21 degrees relative to the longitudinal axis (A) of reciprocal movement between the metering valve (17) and the aerosol container (16). The leaf spring (260) additional urges the counter ring to its upper most vertical position. Engagement of the aforementioned regions together with the bias provided by the dose counter spring prevents the counter ring and count-indicating ring from undergoing any rotational movement during storage and handling. The ferrule (18) may be resting on the circumferential ridge (236) of the indexing member (230) and the saw tooth projections (235) of the indexing member may be resting on the inner ring teeth (241) of the counter ring (240).

As the user presses down on the aerosol container (16) to initiate actuation of the inhaler (5), the downward vertical movement of the aerosol container towards the nozzle block (21) causes the ferrule (18) to engage (if it has not already done so) and then push down on the circumferential ridge (236) of the indexing member (230), thus causing a downward vertical movement of the indexing member and thus initiating the outward stroke of the indexing member. Then, the saw-tooth projections (235) of the indexing member (230) engage (if they have not already done so) and push down on the inner ring teeth (241) of the counter ring (240). These regions of interaction are favourably configured to have opposing angular surfaces and are arranged such that when force is applied, the saw-tooth projections (235) and inner teeth ring (241) urge the counter ring (240) to rotate. However, at first, the ratchet members (224) and the outer teeth ring (244) (i.e. the vertical surfaces of each (225 and 247), respectively) are still engaged, limiting any rotational movement of the counter ring (240). Hence the applied force induces the indexing member (230) to move vertically downwards, and the indexing member in turn induces the counter ring (240) to move in a downwards, vertical or essentially vertical direction against the opposing force from the leaf spring biasing element (260). As the counter ring (240) moves vertically or essentially vertically downwards, the counter ring protrusions (246) also move correspondingly vertically downwardly, causing the count-indicating ring (250) to undergo a first rotational (or essentially rotational) movement under force transmitted from the user, facilitating the breaking away of any accumulations resulting from washing and thus facilitating proper operation of the dose counter. The first such movement of the counter ring (240) induces such a first movement of the count-indicating ring (250), because the protrusions (246) on the counter ring are engaged with channels provided on the count-indicating ring that are inclined.

Figure 6C:
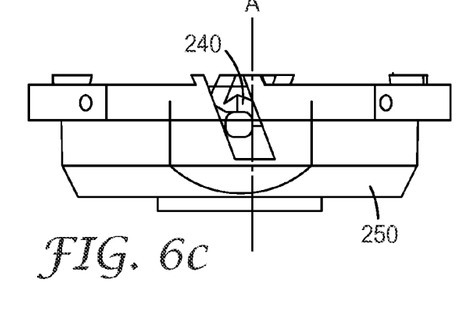
Figure 6D:
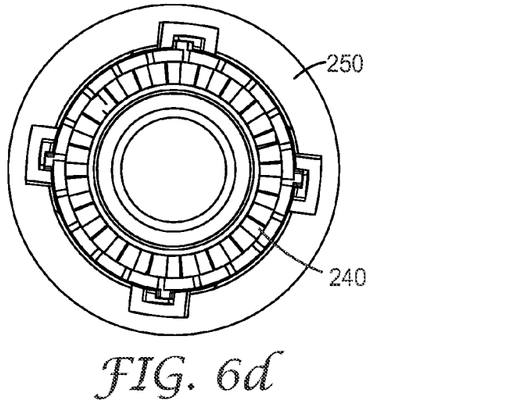

While the patient continues to press down on the aerosol container (16), the indexing member (230) and counter ring (240) continue to move downwardly and the count-indicating ring (250) continues its rotational movement in coordination with the vertical movement of the counter ring—until such time as the counter ring's outer teeth (244) disengage from the ratchet members (224) (in particular until the vertical surfaces of each (247 and 225, respectively) disengage). As mentioned supra, upon disengagement a dose count is committed to and is therefore non-reversible. Furthermore, upon disengagement the counter ring is free to rotate and will rotate under the force of the bias. If applicable (i.e. if the user continues to press down on the container to complete actuation of the inhaler), the counter ring will also continue to move vertically downward under the force of the user via the indexing member. As mentioned above, the regions of interaction of the indexing member (230) and the counter ring (240) include the saw-tooth projections (235) of the indexing member (230) and the inner teeth ring (241) of the counter ring (240). The angular surfaces of said regions (235 and 241) are configured and arranged such that when force is applied by a bias, e.g. the leaf spring (260), the regions are urged vertically towards each other and since the indexing member (230) cannot rotate, the interaction between the saw-tooth projections (235) and inner teeth ring (241) now causes the counter ring (240) to rotate. Rotational movement of the counter ring (240) and thus the rotational movement of the counter ring protrusions (246) within the channels (256) of the count-indicating ring (250) induces the count-indicating ring (250) to undergo further rotational movement. At this stage, the count-indicating ring rotates essentially in tandem with the rotational movement of the counter ring. Once again, if applicable the counter ring may simultaneously move vertically, so that the movement in total is an essentially helical movement; however it is generally the rotational component that induces the rotational movement of the count-indicating ring. FIGS. 6(c) and (d) show the relative positions of the counter ring (240) and the count-indicating ring (250) at the position of the dose counter just after the disengagement, where (c) shows the view from the side where the count-indicating ring is in part sectioned to show better the channel and (d) shows the view from the top. (This position is a position between the schematic representations shown in FIGS. 2(c) and (d).) Comparing FIG. 6(c) to FIG. 6(a), it can be recognized that the counter ring protrusion (246), and thus the counter ring (240), has moved vertically downwards, and comparing the positions of the protrusion(s) and the inclined channel(s) (256) of the count-indicating ring (250) in FIGS. 6 (a) & (b) to FIGS. 6 (c) & (d), it can be the recognized that the counter ring and count-indicating ring have moved rotationally (to the left in the orientation shown in FIGS. (a) & (c) and clockwise in FIGS. (b) & (d).)

Figure 6E:
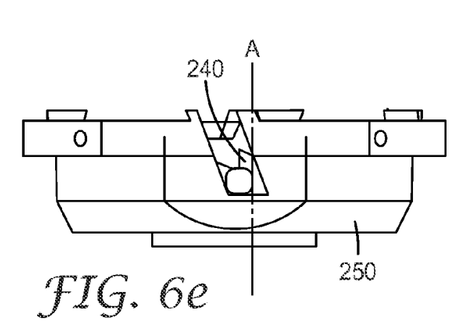
Figure 6F:
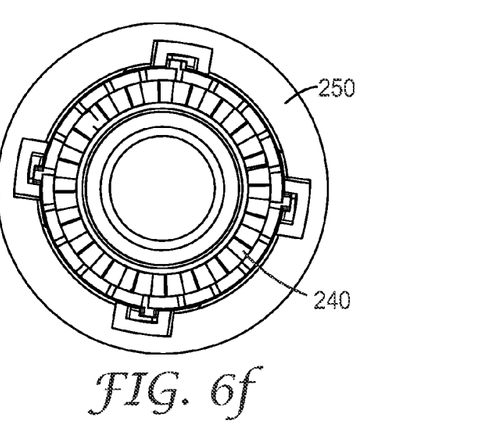

The patient will typically continue to apply force to the aerosol container (16) until a metered dose is released. Typically this will occur shortly after the disengagement described above, to ensure that the dose count has been committed to prior to releasing medicament and hence minimizing any potential to under-count administered doses. After the medicament has been released, the user may (and most often does) continue to apply force onto the aerosol container, thus inducing a continued outward stroke of the indexing member (230). This movement is however generally not necessary for the dose counter to complete its counting motion. During this movement, the counter ring (240) generally moves vertically downwards until the protrusions of the counter ring reach the bottoms of the inclined channels (256) of the count-indicating ring (250). In other words, the counter ring protrusions bottom out, and movement, i.e. rotational movement, of the counter ring and count-indicating ring ceases. FIGS. 6(e) and (f) shown the relative positions of the counter ring (240) and the count-indicating ring (250) at the position of the dose counter where the protrusions (246) of the counter ring (240) are bottomed out, where (e) shows the view from the side where the count-indicating ring is in part sectioned to show better the channel and (f) shows the view from the top. (This position is a position in the sequence of operation between the schematic representations shown in FIGS. 2(d) and (e).)

When the user of the inhaler releases pressure on the aerosol container (16), the force on the indexing member is released and the indexing member is allowed to commence its return stroke. Moreover, the counter ring (240) is urged, under the force of the leaf spring (260), vertically upwards towards the ratchet member (224), thereby moving the indexing member (230) vertically upwards. As the counter ring continues to move vertically upwardly, the inclined surfaces (226) of the ratchet members (224) and the inclined surfaces (248) of the outer ring of teeth (244) of the counter ring (240) engage. The two sets of inclined surfaces (226, 248) are configured and arranged such that as the counter ring (240) undergoes a further vertically upward movement under the resultant force of the spring (260), the engagement and sliding of said inclined surfaces of the counter ring over the inclined surfaces of the fixed ratchet members (224) induces further rotational movement of the counter ring (240). The last rotational movement of the counter ring allows for completion of a predetermined counting motion. The rotational (and vertical) movement of the counter ring (240), and thus the rotational movement of the counter ring protrusions (246) within the channels (256) of the count-indicating ring (250), induces the count-indicating ring (250) to undergo in tandem a further rotational movement allowing the count-indicating ring to complete a predetermined indicating motion. As the counter ring moves vertical upwards and rotates to complete its predetermined counting motion, the indexing member is continually moved vertically upwards and moves over a tooth of the inner set of teeth (241). The indexing member (230), leaf spring (260) and counter ring (240) return to a second rest position where each set of teeth (241, 244) of the counter ring has been incremented by one tooth and the count-indicating ring (250) and indicia (216) thereon have also been incremented (up or down, as determined by the order of the indicia) (i.e. rotated) by one count.

As mentioned supra, the exemplary dose counter illustrated in FIG. 3 may include a tens cone (270) that is rotated as a function of rotation of the count-indicating ring (250). As mentioned supra, radial spokes (274) of the tens cone are generally arranged such that they may interact with one of two bosses (not visible in FIG. 3) on the outer circumferential cylinder (252) of the count-indicating ring (250). In particular, during every 10th and 20th movement of the count-indicating ring (250), one of the two mentioned bosses engages with a radial spoke (274), causing the tens cone (270) to rotate incrementally about its axis 271 so as to display the next consecutive indicium (217) in the window (215) after every tenth actuation.

The above described exemplary embodiment of a dose counter is described with reference to a pressurized metered dose inhaler. However it will be apparent to a person skilled in the art that the dose counter may be adapted for use with other actuators, dispensers or inhalers having a reciprocal actuation means, for example, nasal pressurized metered dose devices, dry powder inhalers or pump spray devices.

Dose counters are generally constructed from plastic components to keep the cost and weight of the dose counter to a minimum whilst maximising its strength and reliability. The exception to this is often biasing elements (which as mentioned supra may be a spring, for example, a coil spring or a leaf spring) which may be formed from a plastic or metal, in particular steel or spring steel. If metal components are used, metallic materials that resist corrosion and/or oxidation are desirably chosen.

The invention claimed is:
1. A dose counter for use with an inhaler comprising a container for medicament equipped with a reciprocal actuation means to dispense a dose of medicament therefrom, the dose counter comprising:
a counter member constructed and arranged to undergo a predetermined counting motion each time a dose is dispensed, the counting motion comprising at least a first vertical or essentially vertical movement;

a count-indicating member constructed and arranged to undergo a predetermined count-indicating motion each time a dose is dispensed, the count-indicating member comprising a first region for interaction with the counter member;

a fixed ratchet member;

an indexing member constructed and arranged to undergo reciprocal movement coordinated with the reciprocal movement between the reciprocal actuation means and the container and to induce at least said first vertical or essentially vertical movement of the counter member;

wherein the counter member is biased towards the ratchet member and/or the indexing member;

wherein the counter member comprises a first region for interaction with the count-indicating member, said first region of the counter member comprising at least one surface that is engaged with at least one surface of said first region of the count-indicating member;

wherein said first region of the counter member and said first region of the count-indicating member are configured and arranged, such that said count-indicating member completes its count-indicating motion in coordination with the counting motion of said counter member and during and induced by said first movement of the counter member the count-indicating member undergoes a rotational or essentially rotational movement;

wherein the counter member comprises a second region for interaction with the ratchet member, said second region comprising at least one surface that is engaged with the ratchet member at the rest position of the dose counter, wherein said at least one surface of second region of the counter member includes a vertical or essentially vertical surface;

wherein the reciprocal movement of the indexing member comprises an outward stroke and a return stroke and wherein the counter member comprises a third region for interaction with the indexing member, said third region comprising at least one inclined surface which is engaged with the indexing member during its outward stroke, thereby causing the counter member to undergo the first vertical or essentially vertical movement against the bias;

wherein said first vertical or essentially vertical movement of the counter member in turn causes a release of the engagement of the counter member from the ratchet member and thus allows for a subsequent rotational or essentially rotational movement of the counter member under the force of the bias and, if applicable, during further outward movement of the indexing member;

wherein the counter member further comprises a fourth region for interaction with the ratchet member, said fourth region comprising at least one inclined surface which is engaged by the ratchet member during the return stroke of the indexing member, thereby causing the counter member to undergo further rotational and vertical movement to complete said predetermined counting motion; and wherein the first region of the counter member or the first region of the count-indicating member comprises at least one channel, while the first region of the opposing count-indicating member or counter member, respectively, comprises at least one protrusion, wherein said at least one channel and said at least one protrusion are constructed and arranged such that at least one surface of said at least one protrusion engages with at least one surface of said at least one channel, wherein said at least one channel is angled at an angle of 1 degree up to and including 60 degrees relative to the longitudinal axis of reciprocal movement between the reciprocal actuation means and the container.

2. A dose counter according to claim 1, wherein the predetermined counting motion of the counter member includes, independently or simultaneously, vertical and rotational movements; and/or the predetermined count-indicating motion of the count-indicating member includes only rotational or essentially rotational movements.

3. A dose counter according to claim 1, wherein said count-indicating member rotates essentially in tandem with rotational or essentially rotational movement(s) of said counter member.

4. A dose counter according to claim 1, wherein the dose counter comprises at least one biasing element, said at least one biasing element including a spring, in particular a coil spring or a leaf spring.

5. A dose counter according to claim 1, wherein the count-indicating member is provided with an indicium or indicia for indicating how many doses or how much medicament is contained in the container and/or how many doses or how much medicament has been dispensed from the container, in particular said indicium or indicia being numeric and/or colour indicium or indicia.

6. A dose counter according to claim 1, wherein the dose counter is washable, in particular washable with tap water.

7. A dose counter according to claim 1, wherein the counter member is a ring, a cylinder, a disk or a cone; and/or the count-indicating member is a ring, a cylinder, a disk or a cone.

8. An actuator for use with or as part of a dispenser, said actuator comprising a dose counter according to claim 1.

9. An actuator according to claim 8, wherein the dose counter is mounted within the interior of the actuator.

10. An actuator according to claim 8, wherein the actuator is washable, in particular washable with tap water.

11. An actuator according to claim 8, wherein the actuator is an actuator for use with a canister including an aerosol container and a metering valve and wherein the dose counter is mounted within the interior of the actuator, such that, in use, the dose counter is generally positioned beneath the container near and/or around a nozzle block of the actuator.

12. A dispenser comprising an actuator according to claim 8.

13. A dispenser according to claim 12, wherein the dispenser is a metered dose dispenser.

14. A dispenser according to claim 12, wherein the dispenser is a metered dose inhaler.

15. A dispenser according to claim 12, wherein the dispenser is a pressurized metered dose inhaler.

* * * * *